United States Patent
Botár et al.

(10) Patent No.: US 10,494,379 B2
(45) Date of Patent: Dec. 3, 2019

(54) 6-OXA-3,9,15-TRIAZA-BICYCLO[9.3.1]
PENTADECA-1(14),11(15),12-TRIENE
DERIVATIVES BASED COMPOUNDS AND
THEIR APPLICATION AS LIGANDS OF
ESSENTIAL METAL ION BASED MRI AND
$^{52}$MN BASED PET CONTRAST AGENTS

(71) Applicant: DEBRECENI EGYETEM, Debrecen (HU)

(72) Inventors: Richárd Botár, Emöd (HU); Zoltán Garda, Túrricse (HU); Tamás Fodor, Miskolc (HU); Ferenc Krisztián Kálmán, Debrecen (HU); Viktória Nagy, Debrecen (HU); Gyula Tircsó, Debrecen (HU); Imre Tóth, Debrecen (HU)

(73) Assignee: DEBRECENI EGYETEM, Debrecen (HU)

( * ) Notice: Subject to any disclaimer, the term of this patent is extended or adjusted under 35 U.S.C. 154(b) by 0 days.

(21) Appl. No.: 15/778,506

(22) PCT Filed: Nov. 25, 2016

(86) PCT No.: PCT/HU2016/000075
§ 371 (c)(1),
(2) Date: May 23, 2018

(87) PCT Pub. No.: WO2017/089849
PCT Pub. Date: Jun. 1, 2017

(65) Prior Publication Data
US 2018/0354969 A1   Dec. 13, 2018

(30) Foreign Application Priority Data

Nov. 26, 2015  (HU) .................................. P1500566
Oct. 18, 2016  (HU) .................................. P1600583

(51) Int. Cl.
*A61K 49/10* (2006.01)
*A61K 51/04* (2006.01)
*C07D 498/08* (2006.01)

(52) U.S. Cl.
CPC .......... *C07D 498/08* (2013.01); *A61K 49/106* (2013.01); *A61K 51/0482* (2013.01)

(58) Field of Classification Search
CPC .. C07D 498/08; A61K 31/439; A61K 49/101; A61K 51/0474; A61K 49/106; A61K 51/0482
See application file for complete search history.

(56) References Cited

U.S. PATENT DOCUMENTS

| | | | |
|---|---|---|---|
| 5,316,756 A | 5/1994 | Gries et al. | |
| 5,334,371 A | 8/1994 | Gries et al. | |
| 5,480,990 A | 1/1996 | Kiefer et al. | |
| 5,693,310 A | 12/1997 | Gries et al. | |
| 8,268,810 B2 | 9/2012 | Port | |
| 2010/0092396 A1 | 4/2010 | Kovacs et al. | |
| 2011/0092806 A1 | 4/2011 | Port et al. | |
| 2014/0206862 A1 | 7/2014 | Green et al. | |
| 2015/0209452 A1 | 7/2015 | Mirica et al. | |
| 2018/0282333 A1 | 10/2018 | Botár et al. | |
| 2018/0344883 A1 | 12/2018 | Botár et al. | |

FOREIGN PATENT DOCUMENTS

| | | |
|---|---|---|
| EP | 0 130 934 | 1/1985 |
| EP | 0 263 059 | 4/1988 |
| WO | 90/11282 | 10/1990 |
| WO | 94/26276 | 11/1994 |
| WO | 99/65905 | 12/1999 |
| WO | 2011/073371 | 6/2011 |

OTHER PUBLICATIONS

Oshchepkov et al., Russian Chemical Bulletin, International Edition, 2011, 60(3), p. 478-485. (Year: 2011).*
International Search Report mailed relative to PCT/HU2016/000675, dated Feb. 6, 2017 (5 pages).
Written Opinion of the International Searching Authority, mailed relative to PCT/HU2016/000075, dated Feb. 6, 2017 (6 pages).
International Search Report mailed relative to PCT/HU2016/000073, dated Apr. 5, 2017 (5 pages).
Written Opinion of the International Searching Authority, mailed relative to PCT/HU2016/000073, dated Apr. 5, 2017 (8 pages).
International Search Report mailed relative to PCT/HU2016/000074, dated Feb. 10, 2017 (4 pages).

(Continued)

*Primary Examiner* — Michael G. Hartley
*Assistant Examiner* — Leah H Schlientz
(74) *Attorney, Agent, or Firm* — Smith, Gambrell & Russell, LLP

(57) ABSTRACT

The one subject of the invention is the compounds of general formula (I), their isomers, their physiologically acceptable salts and/or Mn(II), Fe(II), Fe(III), Co(II) and Ni(II) complexes and their application: where $R_1$=—OH or —NR$_3$R$_4$ amide functionality.

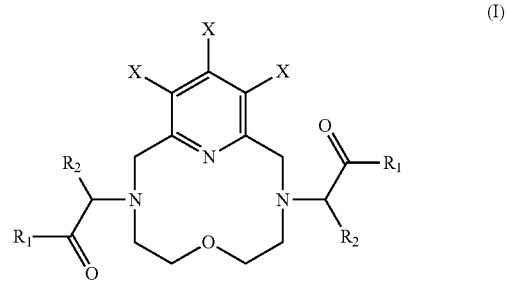

(I)

20 Claims, No Drawings

(56) References Cited

OTHER PUBLICATIONS

Written Opinion of the International Searching Authority, mailed relative to PCT/HU2016/000074, dated Feb. 10, 2017 (6 pages).
Kim, W.D,, et al, Synthesis, Crystal Structure, and Potentiometry of Pyridine-Containing Tetraaza Macrocyclic Ligands with Acetate Pendant Arms. Inorganic Chemistry. 1995. vol. 4, pp. 2225-2232.
Rojas-Quijano, F.A., et at Lanthanide(III) Complexes of Tris(amide) PCTA Derivatives as Potential Bimodal Magnetic Resonance and Optical Imaging Agents. Chemistry. — A European Journal, 2009, vol. 15, pp. 13188-13200.
Weber, E., et al. Ligandstruktur und Kompiexierung, $V^I$) Neue Kronenäther und ihre Alkalimetallion-Komplexe. [Ligand Structure and Complexation, $V^I$) New Crown Ethers and Their Alkali Metal Ion Complexes]. Chemische Berichte, 1976. vol. 109, No. 5, pp. 1803-1831 (with partial English translation).
Aime, S. et al, Designing Novel Contrast Agents for Magnetic Resonance Imaging. Synthesis and Relaxometric Characterization of three Gadolinium(III) Complexes Based on Functionalized Pyridine-Containing Macrocyclic Ligands. Helvetica Chimica Acta. 2003. vol. 86, pp. 615-632.

\* cited by examiner

6-OXA-3,9,15-TRIAZA-BICYCLO[9.3.1] PENTADECA-1(14),11(15),12-TRIENE DERIVATIVES BASED COMPOUNDS AND THEIR APPLICATION AS LIGANDS OF ESSENTIAL METAL ION BASED MRI AND $^{52}$MN BASED PET CONTRAST AGENTS

Subject of the invention is new substituted 6-oxa-3,9,15-triaza-bicyclo[9.3.1]pentadeca-1(14), 11(15),12-triene derivatives and their application as ligands of Mn(II), Fe(II), Fe(III), Co(II) and Ni(II) based MRI contrast agents and $^{52}$Mn based Positron Emission Tomography (PET) contrast agents.

The compounds of the general formula (I) are:

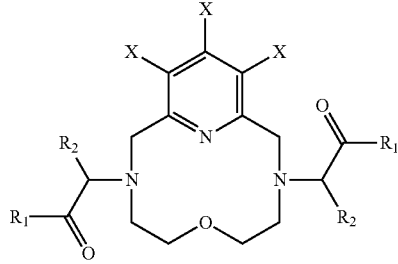

(I)

where $R_1$=—OH or —$NR_3R_4$, wherein —$NR_3R_4$ may refer to:

a). —$NR_3R_4$ means a ring of 4 to 7 members with enclosed N atom, that in certain cases may contain another heteroatom, and in specific cases the ring may be replaced with an aryl group (of 5 to 7 carbon atoms) substituted with —COOH, —OH, —OCH$_3$, —NO$_2$, —NH$_2$, —NCS, —NHS-activated ester, aryl (of 5 to 7 carbon atoms), or nitro-, amino- or isothiocyanate group, or b). in the —$NR_3R_4$ group $R_3$ means a H atom, alkyl (of 1 to 6 carbon atoms), aryl, nitroaryl, aminoaryl or isothiocyanate-aryl group and $R_4$ is a H atom, alkyl (of 1 to 6 carbon atoms) or —(CH$_2$)$_n$—COOH group, whereas n=1 to 10 integer, or c). —$N_3R_4$ group is one of the following groups:

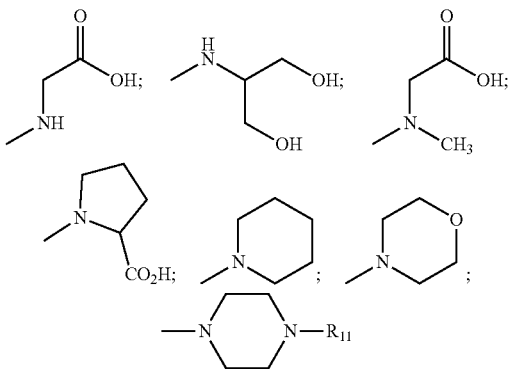

wherein $R_{11}$ is a H atom, carboxyl- or alkyl-carbonyl group (of 1 to 4 carbon atoms);

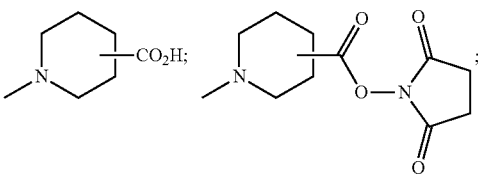

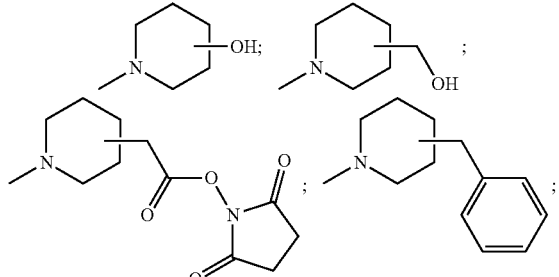

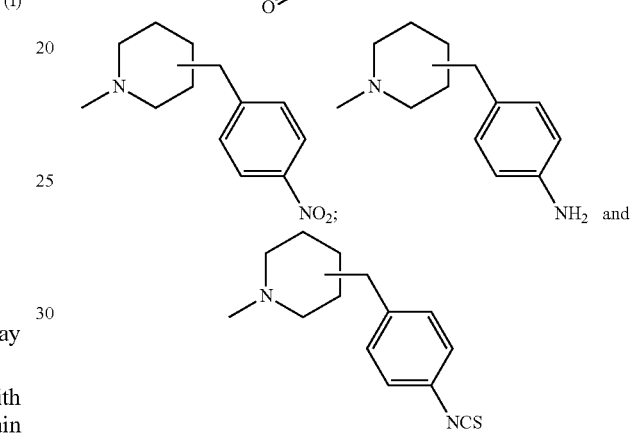

$R_2$ is a H atom or alkyl (of 1 to 6 carbon atoms) aryl, nitroaryl, aminoaryl or isothiocyanate-aryl group.
and
X means independently from one another H atom, —CH$_3$, —COOH, —OH, —OCH$_3$, alkoxy- (of 2 to 6 carbon atoms), —NO$_2$, —NH$_2$, —NCS, —NHS-activated ester, alkyl (of 2 to 12 carbon atoms) or aryl (of 5 to 7 carbon atoms) group, in certain cases the latter may be substituted with hydroxyl, hydroxyalkyl (of 1 to 6 carbon atoms), nitro, amino or isothiocyanate group.

Mn(II), Fe(II), Fe(III), Co(II), and Ni(II) complexes of compounds of general formula (I) can be applied beneficially in MRI ($T_1$ or ParaCEST agents) as contrast agents and $^{52}$Mn based PET diagnostics.

The majority of contrast agents applied in MRI diagnostics are complexes of paramagnetic Gd(III) ion with different ligands. An important disadvantage of Gd(III) containing contrast agents is the toxicity of Gd(III) ion, therefore very strict requirements shall be fulfilled for their application as contrast agent. Nephrogenic Systemic Fibrosis (NSF) discovered in the beginning of the 21$^{st}$ century and associated with the use of Gd(III) containing contrast agents in patients with severe renal disease pointed out that problems may arise due to the use of toxic Gd(III) even in spite of the strict requirement system. Furthermore, the negative outcome of using high quantities of Gd(III) based contrast agents. e.g. gadolinium accumulating in surface waters and coming from clinical waste waters also poses an increasing problem.

The only contrast agent without Gd(III) used in practice was Mangafodipir (Tesalscan) with Mn(II) ion as the central paramagnetic ion, but this was withdrawn from the European market some years ago.

One possibility to decrease the toxicity of the agents is to replace Gd(III) by an essential paramagnetic (such as Mn(II), Fe(II), Fe(III)) metal ion in the contrast agents. Since Mn(II) ion is an essential metal ion, thus appropriate routes for elimination of Mn(II) ion are available in living organisms. Mangafodipir mentioned above can be applied in liver diagnostics due to the different Mn(II) uptake of the healthy and abnormal hepatocytes. In case of Mangafodipir contrast agent, the Mn(II) ions released after dissociation of the complex are taken up possibly due to low kinetic inertness of the complex. At the same time, however, publications are available to support, that despite the endogenic nature of the Mn(II) ion, extended expositions and high doses may cause neurodegenerative changes with Parkinson-like symptoms. Therefore it is more safe to use Mn(II), Fe(II), Fe(III) ion containing contrast agents (complexes) not dissociating or dissociating only at a very small extent while the complex is excreted form the body. The kinetic inertness of Co(II) and Ni(II) ion based contrast agents are also important for very similar reasons.

During the research of Mn(II) ion based Magnetic Resonance Imaging (MRI) contrast agent, synthesis of a macrocycle based complexes applicable as contrast agents in MRI have not been succeeded yet. It is obviously due to the small contrast enhancement effect of complexes caused by the lack of water molecule bound directly to the metal ion. To solve this problem, we managed to design and synthesis macrocyclic ligands, the Mn(II) complexes of which preserve the good equilibrium and kinetic properties, while their relaxation properties fulfil the requirements related to MRI contrast agents owing to the water molecule is present in the inner coordination sphere.

Together with other documents, the EP 130934 European review document describes Mn(II) ion containing contrast agents and substituted tetraacetic-acid-bis(amide) type ligands suitable for the preparation of the mentioned contrast agents, describing trans-1,2-cyclohexanediamine-tetraacetic acid (CDTA)-bis(amide) derivatives and their Mn(II), Fe(II), Fe(III), Co(II), and Ni(II) complexes.

The EP 263059 European review document provides additional similar compounds as derivatives of the trans-1,2-cyclohexanediamine-tetraacetic acid-bismethyl-amide and bis(3-oxa-pentamethylene)-carboxamide.

The US 2011/0092806 published document describes 'chelate-linker-biovector' type associates for application in diagnostic imaging having DPTA, DOTA, NOTA, DO3A and PCTA basic structure or their derivatives.

The WO 2011/073371 international publication refers to substituted 3,6,9,15-tetraazabicyclo[9.3.1]pentadecatriene derivatives and the Mn(II) complexes of the same carrying acetic acid ester group on the basic structure.

In our research, the main goal was to develop Mn(II), Fe(II), Fe(III), Co(II) and Ni(II) ion based complexes of high relaxivity and high kinetic inertness for their application as contrast agents in MRI as well as $^{52}$Mn based PET diagnostics.

In our experiments, the 6-oxa-3,9,15-triaza-bicyclo[9.3.1]pentadeca-1(14),11(15),12-triene macrocyclic compounds with general formula (I) were found favourable as complex forming agents of new type contrast agents.

Synthesis of compounds of the invention is shown in the following examples:

EXAMPLE 1

Synthesis of tOPC2A

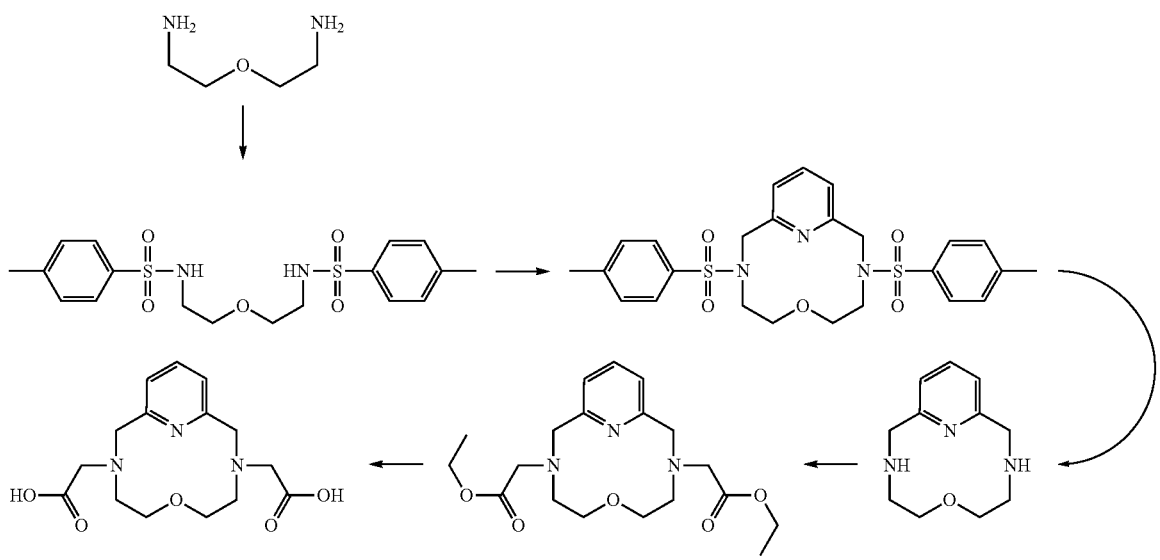

a). Bis-(2-tosylaminoethyl)-ether

The commercially available Bis-(2-aminoethyl)-ether (5.50 g, 5.28 mmol, 1 equivalent) was dissolved in 50 ml water. The pH of the solution was adjusted to 12 by using solid NaOH. Tosyl chloride (22.85 g, 12.03 mmol, 2.27 equiv.) was dissolved in diethyl ether and added dropwise to the vigorously stirred aqueous solution of amine. After evaporation of the ether a brownish precipitate formed which was collected by careful decantation of the remaining aqueous solution. The yellowish precipitate was dissolved in 20 mL mixture of methanol and chloroform (1:9 ratio by volume) and purified by flash chromatography on silica gel. The fraction containing the desired product was evaporated under reduced pressure and the residue was recrystallized twice from ethanol. Yield: 4.85 g (30.7%). $^1$H NMR (CDCl₃): δ 2.42 (s, 6H), 3.07 (m, 4H), 3.37 (t, 4H), 5.26 (t, 2H), 7.30 (d, 4H), 7.75 (d, 4H).

b). 4-oxo-1,7-diaza-2,6-pyridinophano-1,7-ditosylate 2,6-bis(bromomethyl)pyridine (0.50 g, 1.893 mmol) in dry CH₃CN (10 mL) was slowly added dropwise over a mixture of bis-(2-tosylaminoethyl)-ether obtained as described above (0.78 g, 1.893 mmol) and K₂CO₃ (2.62 g, 18.93 mmol, 10 equivalent) in refluxing CH₃CN (10 mL) under argon for 22 h. Then the solution was filtered, and the solid was washed thoroughly with excess of CH₃CN. The combined organic layers were concentrated in a vacuum to give a white solid. The crude product was dissolved in small amount of chloroform (5 mL) and boiling ethanol was added to the solution (25 mL) until the solution became cloudy. Small sized white crystals were obtained on keeping the solution in the fridge at 4° C. Yield: 0.58 g (59.6%).

¹H NMR (CDCl₃, 360 MHz): δ 2.44 (s, 6H), 3.26 (t, 4H), 3.33 (t, 4H), 4.38 (s, 4H), 7.29 (d, 2H), 7.34 (d, 4H), 7.66 (t, 1H), 7.75 (d, 4H).

c). 4-oxo-1,7-diaza-2,6-pyridinophane

In a small beaker the 4-oxo-1,7-diaza-2,6-pyridinophano-1,7-ditosylate (2.27 g, 4.41 mmol) was dissolved in cc. H₂SO₄ (7.5 mL) and it was heated at 180° C. while stirred continuously. The reaction mixture was kept at this temperature for 5 minutes, then it was cooled down first to room temperature and later further to 0° C. by using water-ice mixture. Cold ether was added to the mixture in small portions applying continuous cooling and mixing which resulted in a precipitate formation. The solvent was decanted from the dihydrogen sulphate salt of the precipitated macrocycle and the residue was dissolved in 20 mL distilled water. The pH of the solution was adjusted to 13.2 by using solid NaOH and the product was extracted tree times with chloroform (20 mL). The organic phase was dried over MgSO₄ and evaporated under vacuum. Yield: 0.41 g (44.9%).

¹H NMR (CDCl₃, 360 MHz): δ 2.71 (t, 4H), 3.05 (t, 4H), 3.88 (s, 4H), 6.95 (d, 2H). 7.48 (t, 1H).

d). 4-oxo-1,7-diaza-2,6-pyridinophane-diacetate (tOPC2A)

The 4-oxo-1,7-diaza-2,6-pyridinophane (0.41 g, 1.98 mmol) and K₂CO₃ (1.10 g, 7.92 mmol, 4 equivalent) was suspended in acetonitrile (15 ml), and then the solution of ethyl bromoacetate (0.70 g, 0.47 ml, 4,158 mmol, 2.1 equivalent) in acetonitrile (5 mL) was added dropwise to the acetonitrile suspension of -oxo-1,7-diaza-2,6-pyridinophane and K₂CO₃. After this the reaction mixture was stirred for one hour at room temperature and another 24 hours at boiling temperature. The mixture was filtered and the solvent was evaporated under reduced pressure. The resulting material was dissolved in chloroform (10 ml) and washed twice with distilled water (2×10 mL). The aqueous phase was washed with CHCl₃ (2×10 mL) and then the unified organic phases were dried with Na₂SO₄ and evaporated to dryness under reduced pressure. The obtained crude product was purified with HPLC (Luna 10u-Prep C18(2) 100A (250×21.20 mm; 10 μm) column), ACN:H₂O/TFA was applied as eluent [ACN: acetonitrile; TFA: trifluoroacetic acid]. TFA was contained only in water in 0.005 M concentration. The yield of the analytically pure product was 0.19 g (25.3%).

¹H NMR (CDCl₃, 360 MHz): δ 1.28 (t, 6H), 3.19 (t, 4H), 3.41 (t, 4H), 3.90 (s, 4H), 4.21 (q, 4H), 4.58 (s, 4H), 7.58 (d, 2H), 8.18 (t, 1H);

¹³C NMR (CDCl₃, 360 MHz): δ 56.08; 56.75; 57.95; 61.66; 67.13; 123.08; 144.02; 152.04; 169.88.

e)

The obtained diethyl ester derivative (0.19 g) was dissolved in absolute ethanol, and then NaOH (50%, 0.15 ml, 3.75 mmol, 7.5 equiv.) was added to the mixture and the solution was refluxed for 18 hours. The reaction mixture was cooled down and the solvent was evaporated off under vacuum. The pH of the residue was dissolved in a small amount of water (2.5 mL) and the pH of the solution was adjusted to 2.0 with the use of 2 M HCl. The tOPC2A crystallized off form the given solution during its storage in the fridge at 4° C. The precipitate was filtered off and washed with small amount of cold distilled water and dried under vacuum to constant weight. Yield: 0.15 g (93.0%).

¹H NMR (D₂O, 360 MHz): δ 2.50 (t, 4H), 2.73 (s br, 4H), 3.20 (s, 4H), 3.71 (s br, 4H), 7.07 (d, 2H), 7.48 (t, 1H);

¹³C NMR (D₂O, 360 MHz): δ 55.38; 61.71; 62.17; 67.28; 120.64; 120.70; 137.90; 158.65; 179.90.

EXAMPLE 2

Synthesis of tOPC2AM$^{Pyp}$ a.) 2-bromo-1-(piperidine-1-yl)ethanone

Bromoacetyl bromide (3.56 g, 17.6 mmol, 1.55 ml, 1.5 equivalent), dry CH₂Cl₂ (50 ml) and K₃PO₄ (6.41 g, 30.2 mmol, 2.5 equivalent) was mixed in a flask of 250 ml under N₂ atmosphere. Piperidine (1.00 g, 11.7 mmol, 1.0 equivalent) was dissolved in dry CH₂Cl₂ (20 ml) and was added dropwise to dichloromethane solution of bromoacetyl bromide at 0° C. in 30 minutes, then the reaction mixture was stirred for additional 12 hours at room temperature under N₂ atmosphere before the aqueous HCl solution (0.5 M, 30 ml) was added to the reaction mixture. After the addition of HCl solution, the reaction mixture was stirred for additional 5 minutes, then the two phases were separated using a separatory funnel. The aqueous phase was washed with CH₂Cl₂ (1×15 ml) and then the unified organic phases were washed with KHCO₃ solution (2×30 ml, 10 m/m %) and saturated NaCl solution (1×30 ml). The organic phase was dried with MgSO₄, then dichloromethane was evaporated at reduced pressure, and the crude product was stored at −20° C. until further use. Yield: 1.73 g (70%).

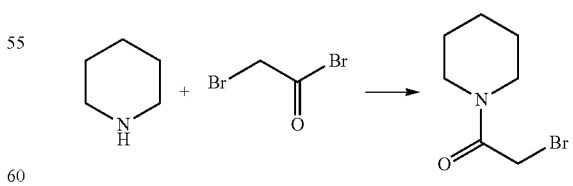

¹H NMR [360 MHz, CDCl₃] δ 1.59 (2H, m, (CH₂) ring), 1.67 (4H, m, (CH₂) ring), 3.45 (2H, t, (CH₂) ring), 3.59 (2H, t, (CH₂) ring), 3.87 (2H, s, (CH₂)), ¹³C NMR [100 MHz, CDCl₃] δ 25.4 (2 pcs CH₂ ring); 26.0 (CH₂ ring); 27.2 (CH₂Br); 44.2 (2 pcs CH₂ ring); 169.5 (C(=O));

b.) Synthesis of tOPC2AM$^{Pyp}$

The 2-bromo-1-(piperidin-1-yl)ethanone obtained as described above (0.36 g, 1.74 mmol, 2.5 equivalent) was dissolved in dry acetonitrile and added dropwise to the acetonitrile solution (30 ml) of 6-oxa-3,9,15-triaza-bicyclo[9.3.1]pentadeca-1(14),11(15),12-triene (0.15 g, 0.72 mmol, 1 equivalent) and K$_2$CO$_3$ (0.30 g, 2.20 mmol, 3 equivalent) at room temperature within 30 minutes. Then the reaction mixture was refluxed in N$_2$ atmosphere for 24 hours. After 24 hours, K$_2$CO$_3$ was filtered from the hot solution, and acetonitrile was evaporated at reduced pressure. The obtained crude product was purified with HPLC (Luna 10u-Prep C18(2) 100A (250×21.20 mm; 10 μm) column), ACN:H$_2$O/TFA was applied as eluent [ACN: acetonitrile; TFA: trifluoroacetic acid]. TFA was contained only in water in 0.005 M concentration. The received compound is 3,9-bis[2-oxo-2-(piperidin-1-yl)-ethyl]-6-oxa-3,9,15-triaza-bicyclo[9.3.1]pentadeca-1(14),11(15),12-triene. Yield: 0.16 g (50%)

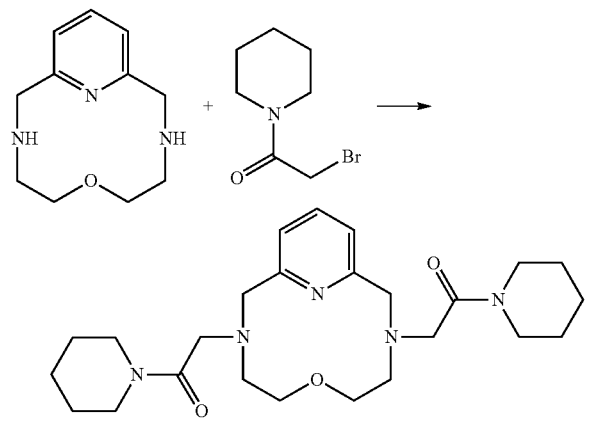

$^1$H NMR [360 MHz, D$_2$O] δ 1.52 (12H, m, (6 pcs CH$_2$)), 3.2 (2H, m, (CH$_2$)), 3.3-3.50 (8H, m, (4 pcs CH$_2$)), 3.85 (2H, m, (CH$_2$)), 4.65 (4H, m, (2 pcs CH$_2$)), 4.81 (4H, s, (2 pcs CH$_2$)), 7.45 (2H, d, (CH) aromatic), 7.95 (1H, t, (CH) aromatic);

$^{13}$C NMR [100 MHz, D$_2$O] δ 23.4 (2 pcs CH$_2$); 25.0 (2 pcs CH$_2$); 25.5 (2 pcs CH$_2$); 43.9 (4 pcs CH$_2$); 46.1 (2 pcs CH$_2$); 57.8 (2 pcs CH$_2$); 60.1 (2 pcs CH$_2$); 64.2 (2 pcs CH$_2$); 122.4 (2 pcs CH aromatic); 140.2 (CH aromatic); 149.3 (2 pcs C aromatic); 162.5 (2 pcs C(=O));

MS (ESI) m/z 458.460 (M+H)$^+$ 100%; 480.500 (M+Na)$^+$ 29%;

IR: 1650 cm$^{-1}$ (>C=O); 2159, 2010 (aromatic >C=C) and 1093 cm$^{-1}$ (≥C—O—C≤);

EXAMPLE 3

Synthesis of tOPC2AM$^{Morf}$

The commercially available 4-(bromoacetyl)morpholine (0.37 g, 1.78 mmol, 2.5 equivalent) was dissolved in dry acetonitrile (5 ml), then added dropwise to the acetonitrile suspension (30 ml) of 6-oxa-3,9,15-triaza-bicyclo[9.3.1]pentadeca-1(14),11(15),12-triene (0.15 g, 0.72 mmol, 1 equivalent) and K$_2$CO$_3$ (0.30 g, 2.20 mmol, 3 equivalent) at room temperature within 30 minutes. Then the reaction mixture was refluxed in N$_2$ atmosphere for 24 hours. After 24 hours, K$_2$CO$_3$ was filtered from the hot solution, and the solvent was evaporated at reduced pressure. The obtained crude product was purified with HPLC (Luna 10u-Prep C18(2) 100A (250×21.20 mm; 10 μm) column), ACN:H$_2$O/TFA was applied as eluent [ACN: acetonitrile; TFA: trifluoroacetic acid]. TFA was contained only in water in 0.005 M concentration. Yield: 0.14 g (42%).

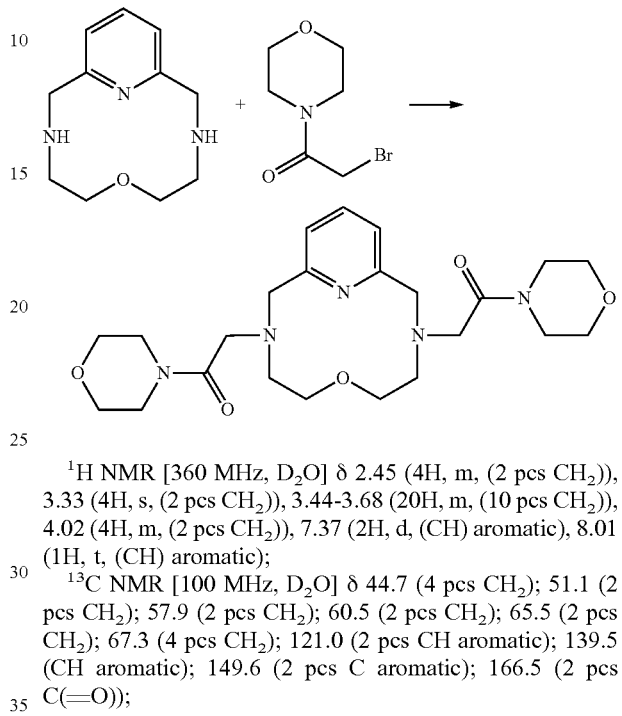

$^1$H NMR [360 MHz, D$_2$O] δ 2.45 (4H, m, (2 pcs CH$_2$)), 3.33 (4H, s, (2 pcs CH$_2$)), 3.44-3.68 (20H, m, (10 pcs CH$_2$)), 4.02 (4H, m, (2 pcs CH$_2$)), 7.37 (2H, d, (CH) aromatic), 8.01 (1H, t, (CH) aromatic);

$^{13}$C NMR [100 MHz, D$_2$O] δ 44.7 (4 pcs CH$_2$); 51.1 (2 pcs CH$_2$); 57.9 (2 pcs CH$_2$); 60.5 (2 pcs CH$_2$); 65.5 (2 pcs CH$_2$); 67.3 (4 pcs CH$_2$); 121.0 (2 pcs CH aromatic); 139.5 (CH aromatic); 149.6 (2 pcs C aromatic); 166.5 (2 pcs C(=O));

EXAMPLE 4

Synthesis of tOPC2AM$^{PipAC}$

The commercially available 1-acetyl-4-(bromoacetyl)piperazine (0.44 g, 1.78 mmol, 2.5 equivalent) was dissolved in dry acetonitrile (5 ml), then added dropwise to the acetonitrile suspension (30 ml) of 6-oxa-3,9,15-triaza-bicyclo[9.3.1]pentadeca-1(14),11(15),12-triene (0.15 g, 0.72 mmol, 1 equivalent) and K$_2$CO$_3$ (0.30 g, 2.20 mmol, 3 equivalent) at room temperature within 30 minutes. Then the reaction mixture was refluxed in N$_2$ atmosphere for 24 hours. After 24 hours, K$_2$CO$_3$ was filtered from the hot solution, and the filtrate was evaporated at reduced pressure. The obtained crude product was purified with HPLC (Luna 10u-Prep C18(2) 100A (250×21.20 mm; 10 μm) column), ACN:H$_2$O/TFA was applied as eluent [ACN: acetonitrile; TFA: trifluoroacetic acid]. TFA was contained only in water in 0.005 M concentration. Yield: 0.13 g (33%).

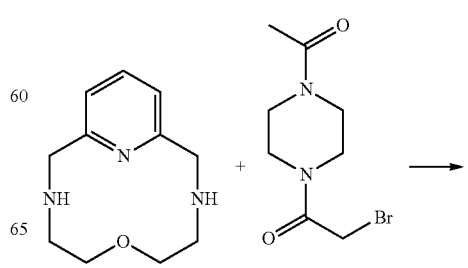

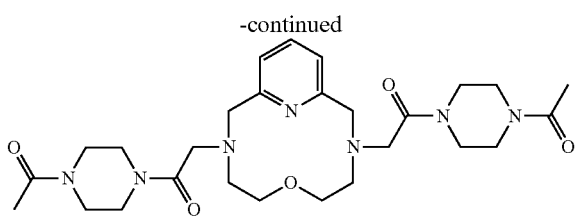

$^1$H NMR [360 MHz, D$_2$O] δ 2.20 (6H, s, (2 pcs CH$_3$)) 2.44 (4H, m, (2 pcs CH$_2$)), 3.31 (4H, s, (2 pcs CH$_2$)), 3.48-3.71 (20H, m, (10 pcs CH$_2$)), 4.04 (4H, m, (2 pcs CH$_2$)), 7.32 (2H, d, (CH) aromatic), 7.92 (1H, t, (CH) aromatic);

$^{13}$C NMR [100 MHz, D$_2$O] δ 23.4 (2 pcs CH$_3$); 44.7 (4 pcs CH$_2$); 53.6 (2 pcs CH$_2$); 54.6 (8 pcs CH$_2$); 61.2 (2 pcs CH$_2$); 62.3 (2 pcs CH$_2$); 66.4 (2 pcs CH$_2$); 122.2 (2 pcs CH aromatic); 140.3 (CH aromatic); 151.3 (2 pcs C aromatic); 168.9 (2 pcs C(=O)); 174.1 (2 pcs C(=O))

EXAMPLE 5

Synthesis of tOPC2AM$^{Pro}$ a.) Tert-butyl 1-(2-bromoacetyl)pyrrolidine-2-carboxylate Bromoacetyl bromide (1.44 g, 7.2 mmol, 0.63 ml, 1.5 equivalent), dry CH$_2$Cl$_2$ (30 ml) and K$_3$PO$_4$ (2.55 g, 12.0 mmol, 2.5 equivalent) was mixed in a flask of 250 ml and stirred under N$_2$ atmosphere. D-proline tert-butyl ester hydrochloride (1.00 g, 4.8 mmol, 1.0 equivalent) was dissolved in dry CH$_2$Cl$_2$ (20 ml) and was added dropwise to dichloromethane solution of bromoacetyl bromide at 0° C. in 30 minutes, then the reaction mixture was stirred for additional 12 hours at room temperature under N$_2$ atmosphere before the aqueous HCl solution (0.5 M, 20 ml) was added to the reaction mixture. After the addition of HCl solution, the reaction mixture was stirred for additional 5 minutes, then the two phases were separated using a separatory funnel. The aqueous phase was washed with CH$_2$Cl$_2$ (1×10 ml) and then the unified organic phases were washed with KHCO$_3$ solution (2×20 ml, 10 m/m %) and saturated NaCl solution (1×20 ml). The organic phase was dried with MgSO$_4$, then dichloromethane was evaporated at reduced pressure, and the crude product was stored at −20° C. until further use. Yield: 1.05 g (75%).

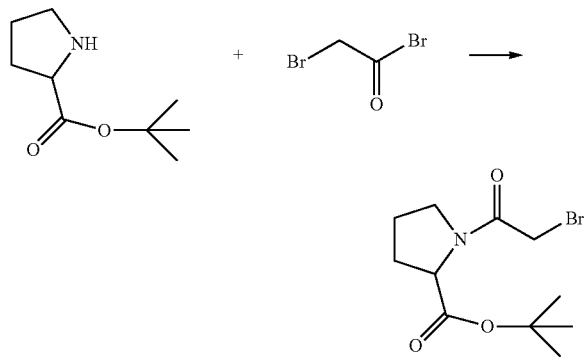

$^1$H NMR [360 MHz, CDCl$_3$] δ 1.60 (9H, s, (CH$_3$)), 2.15 (2H, m, (CH$_2$) ring), 2.43 (2H, m, (CH$_2$)ring), 3.72 (2H, m, (CH$_2$) ring), 4.00 (2H, s, (CH$_2$)), 4.55 (1H, m, (CH) ring);

$^{13}$C NMR [100 MHz, CDCl$_3$] δ 25.0 CH$_2$ ring; 27.0 CH$_2$Br; 28.0 (3C CH$_3$); 29.2 CH$_2$ ring; 47.5 CH$_2$ ring; 60.2 CH ring; 81.8 CH t-butyl; 165.2 C(=O); 170.9 C(=O);

b.) Synthesis of tOPC2AM$^{Pro}$

The tert-butyl 1-(2-bromoacetyl)pyrrolidine-2-carboxylate obtained as described above (0.35 g, 1.20 mmol, 2.5 equivalent) was dissolved in dry acetonitrile (20 ml) and added dropwise to the acetonitrile solution of 6-oxa-3,9,15-triaza-bicyclo[9.3.1]pentadeca-1(14),11(15),12-triene (0.10 g, 0.48 mmol, 1 equivalent) and K$_2$CO$_3$ (0.20 g, 1.50 mmol, 3 equivalent) at room temperature within 30 minutes. Then the reaction mixture was refluxed in N$_2$ atmosphere for 24 hours. After 24 hours, K$_2$CO$_3$ was filtered from the hot solution, and acetonitrile was evaporated at reduced pressure. The obtained yellowish oil was dissolved in CH$_2$Cl$_2$ (10 ml), then trifluoroacetic acid is added to it (0.25 ml, 6 equivalent) and the reaction mixture was refluxed for 24 hours. The obtained crude product was purified with HPLC (Luna 10u-Prep C18(2) 100A (250×21.20 mm; 10 μm) column), ACN:H$_2$O/TFA was applied as eluent [ACN: acetonitrile; TFA: trifluoroacetic acid]. TFA was contained only in water in 0.005 M concentration. Yield: 0.15 g (60%).

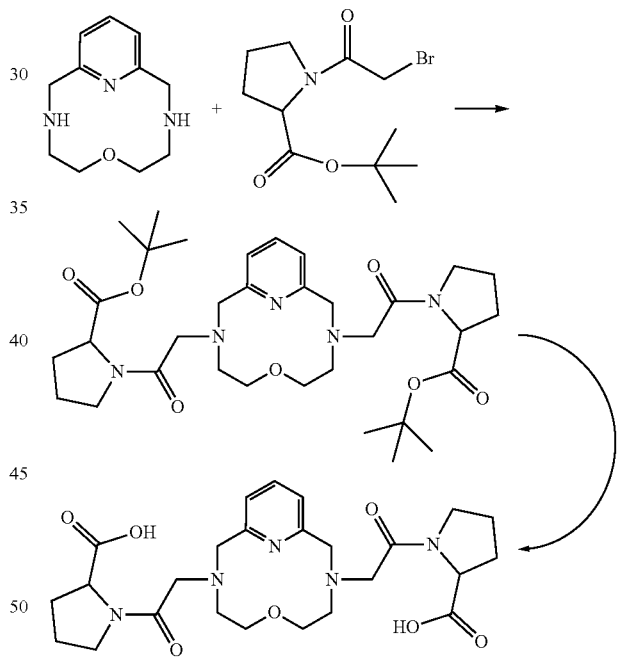

$^1$H NMR [360 MHz, D$_2$O] δ 1.75-2.20 (8H, m, (CH$_2$)), 2.90 (2H, s, (CH$_2$)), 3.3-3.75 (10H, m, (CH$_2$)), 4.15-4.55 (6H, m, (2 pcs CH$_2$ and 2 pcs CH)), 4.65 (4H, s, (CH$_2$)), 7.25 (2H, d, (CH) aromatic), 7.75 (1H, t, (CH) aromatic);

$^{13}$C NMR [100 MHz, D$_2$O] δ 24.3 (2 pcs CH$_2$); 28.8 (2 pcs CH$_2$); 46.8 (2 pcs CH$_2$); 57.8 (2 pcs CH$_2$); 58.1 (2 pcs CH$_2$); 59.5 (2 pcs CH$_2$); 59.8 (2 pcs CH$_2$); 63.9 (2 pcs CH); 122.3 (2 pcs CH aromatic); 140.1 (CH aromatic); 149.2 (2 pcs C aromatic); 163.7 (2 pcs C(=O)); 175.1 (2 pcs C (COOH));

MS (ESI) m/z 518.44 (M+H)$^+$ 100%; 540.470 (M+Na)$^+$ 20%;

IR: 1721, 1644 cm$^{-1}$ (>C=O); 2175, 1996 (aromatic >C=C) and 1094 cm$^{-1}$ (≥C—O—C≤);

EXAMPLE 6

Synthesis of tOPC2AM$^{Sar}$ a.) N-(bromoacetyl)sarcosine Tert-butyl Ester

Bromoacetyl bromide (3.56 g, 17.6 mmol, 1.55 ml, 1.5 equivalent), dry $CH_2Cl_2$ (50 ml) and $K_3PO_4$ (6.41 g, 30.2 mmol, 2.5 equivalent) was mixed in a flask of 250 ml under $N_2$ atmosphere. Sarcosine tert-butyl ester (1.7 g, 11.7 mmol, 1.0 equivalent) was dissolved in dry $CH_2Cl_2$ (20 ml) and was added dropwise to dichloromethane solution of bromoacetyl bromide at 0° C. in 30 minutes, then the reaction mixture was stirred for additional 12 hours at room temperature under $N_2$ atmosphere before the aqueous HCl solution (0.5 M, 30 ml) was added to the reaction mixture. After the addition of HCl solution, the reaction mixture was stirred for additional 5 minutes, then the two phases were separated using a separatory funnel. The aqueous phase was washed with $CH_2Cl_2$ (1×15 ml) and then the unified organic phases were washed with $KHCO_3$ solution (2×30 ml, 10 m/m %) and saturated NaCl solution (1×30 ml). The organic phase was dried with $MgSO_4$, then dichloromethane was evaporated at reduced pressure, and the crude product was stored at −20° C. until further use. Yield: 2.01 g (65%).

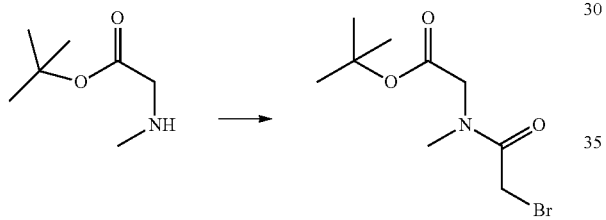

$^1$H NMR [360 MHz, $CDCl_3$] δ 1.6 (9H, s, $CH_3$) 2.8 (3H, s, $CH_3$), 4.01 (2H, s, $CH_2$), 4.4 (2H, s, $CH_2$)

b). Synthesis of tOPC2AM$^{Sar}$

The N-(bromoacetyl)sarcosine tert-butyl ester obtained as described above (0.32 g, 1.20 mmol, 2.5 equivalent) was dissolved in dry acetonitrile (20 ml) and added dropwise to the acetonitrile solution of 6-oxa-3,9,15-triaza-bicyclo[9.3.1]pentadeca-1(14),11(15),12-triene (0.10 g, 0.48 mmol, 1 equivalent) and $K_2CO_3$ (0.20 g, 1.50 mmol, 3 equivalent) at room temperature within 30 minutes. Then the reaction mixture was refluxed in N2 atmosphere for 24 hours. After 24 hours, $K_2CO_3$ was filtered from the hot solution, and acetonitrile was evaporated at reduced pressure. The obtained yellowish oil was dissolved in $CH_2Cl_2$ (10 ml), then trifluoroacetic acid is added to it (0.25 ml, 6 equivalent) and the reaction mixture was refluxed for 24 hours. The obtained crude product was purified with HPLC (Luna 10u-Prep C18(2) 100A (250×21.20 mm; 10 μm) column), ACN:$H_2$O/TFA was applied as eluent [ACN: acetonitrile; TFA: trifluoroacetic acid]. TFA was contained only in water in 0.005 M concentration. Yield: 0.15 g (67%). $^1$H NMR [360 MHz, $D_2O$] δ 7.91 (1H, t, aromatic), 7.31 (2H, d, aromatic) 4.87 (4H, s, $CH_2$), 4.11 (4H, s, $CH_2$), 3.54 (6H, s, $CH_3$), 3.61 (4H, t, $CH_2$), 3.34 (4H, s, $CH_2$), 2.61 (4H, t, $CH_2$).

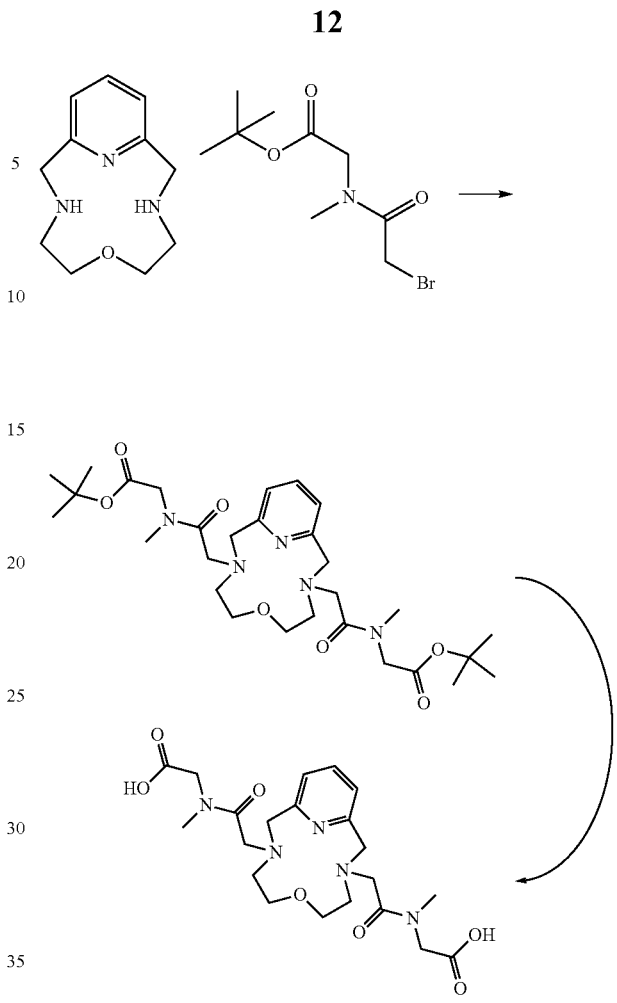

EXAMPLE 7

Synthesis of tOPC2AM$^{PypCOOH}$ a.) N-(bromoacetyl)piperidine-4-carboxylic Acid Tert-butyl Ester

Bromoacetyl bromide (3.56 g, 17.6 mmol, 1.55 ml, 1.5 equivalent), dry $CH_2Cl_2$ (50 ml) and $K_3PO_4$ (6.41 g, 30.2 mmol, 2.5 equivalent) was mixed in a flask of 250 ml under $N_2$ atmosphere. Piperidine tert-butyl ester (2.2 g, 11.7 mmol, 1.0 equivalent) was dissolved in dry $CH_2Cl_2$ (20 ml) and was added dropwise to dichloromethane solution of bromoacetyl bromide at 0° C. in 30 minutes, then the reaction mixture was stirred for additional 12 hours at room temperature under $N_2$ atmosphere before the aqueous HCl solution (0.5 M, 30 ml) was added to the reaction mixture. After the addition of HCl solution, the reaction mixture was stirred for additional 5 minutes, then the two phases were separated using a separatory funnel. The aqueous phase was washed with $CH_2Cl_2$ (1×15 ml) and then the unified organic phases were washed with $KHCO_3$ solution (2×30 ml, 10 m/m %) and saturated NaCl solution (1×30 ml). The organic phase was dried with $MgSO_4$, then dichloromethane was evaporated at reduced pressure, and the crude product was stored at −20° C. until further use. Yield: 2.1 g (59%).

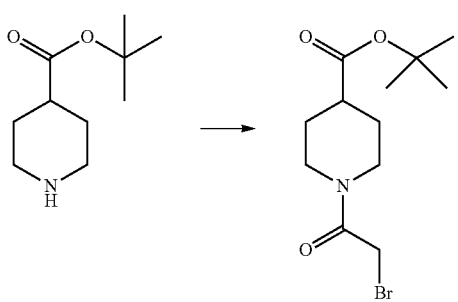 [SMILES: CC(C)(C)OC(=O)C1CCNCC1 ; CC(C)(C)OC(=O)C1CCN(C(=O)CBr)CC1]

¹H NMR [360 MHz, CDCl₃] δ 1.50 (9H, s, CH₃) 2.50 (1H, s, CH), 4.01 (2H, s, (CH₂), 3.5-1.6 (8H, m, CH₂), 4.31 (2H, s, CH₂)

b.) Synthesis of tOPC2AM$^{PypCOOH}$

The N-(bromoacetyl)piperidine tert-butyl ester obtained as described above (0.37 g, 1.20 mmol, 2.5 equivalent) was dissolved in dry acetonitrile (20 ml) and added dropwise to the acetonitrile solution of 6-oxa-3,9,15-triaza-bicyclo [9.3.1]pentadeca-1(14),11(15),12-triene (0.10 g, 0.48 mmol, 1 equivalent) and K₂CO₃ (0.20 g, 1.50 mmol, 3 equivalent) at room temperature within 30 minutes. Then the reaction mixture was refluxed in N₂ atmosphere for 24 hours. After 24 hours, K₂CO₃ was filtered from the hot solution, and acetonitrile was evaporated at reduced pressure. The obtained yellowish oil was dissolved in CH₂Cl₂ (10 ml), then trifluoroacetic acid is added to it (0.25 ml, 6 equivalent) and the reaction mixture was refluxed for 24 hours. The obtained crude product was purified with HPLC (Luna 10u-Prep C18(2) 100A (250×21.20 mm: 10 μm) column), ACN:H₂O/TFA was applied as eluent [ACN: acetonitrile; TFA: trifluoroacetic acid]. TFA was contained only in water in 0.005 M concentration. Yield: 0.17 g (65%).

¹H NMR [360 MHz, D₂O] δ 7.91 (1H, t, aromatic), 7.34 (2H, d, aromatic) 4.11 (4H, s, CH₂) 3.47 (4H, m, CH₂) 3.43-3.17 (8H, m, CH₂) 3.34 (4H, s, CH₂) 2.61 (4H, t, CH₂), 2.32 (2H, CH) 1.89-1.60 (12H, m, CH₂)

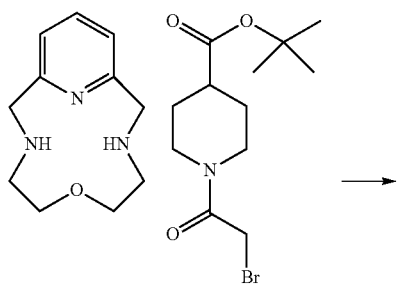

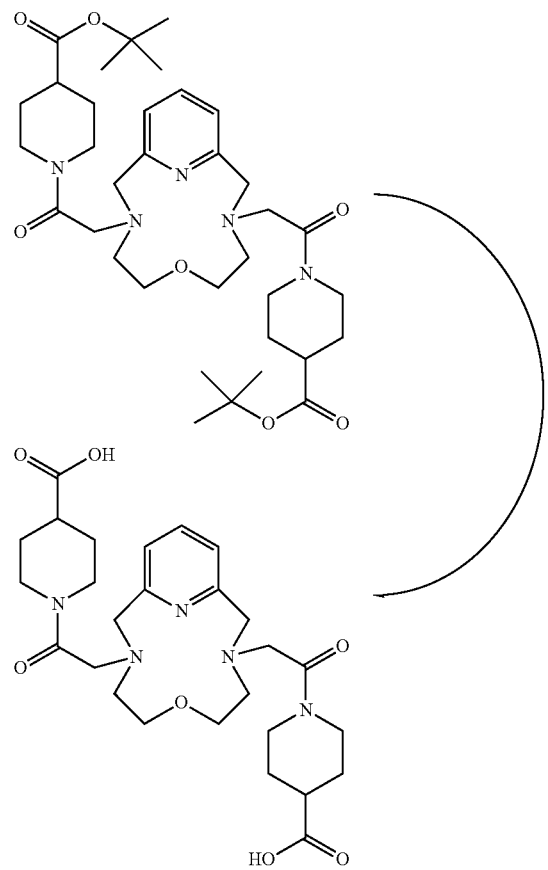

EXAMPLE 8

Manufacture of tOPC2AM$^{PypCOONHS}$

The tOPC2AM$^{PypCOOH}$ (0.20 g, 0.37 mmol, 1.0 equivalent) obtained as described above was dissolved in dry DMF, then DCC (0.15 g, 0.74 mmol, 2 equ.) was added at room temperature and the reaction mixture was stirred at room temperature for 2 hours. Then NHS (N-Hydroxysuccinimide) (0.09 g, 0.73 mmol, 2 equ.) was added and the reaction mixture was stirred for additional 20 hours. When the reaction time was elapsed, the precipitate was filtered, and the filtrate was evaporated at reduced pressure. The obtained crude product was purified with HPLC (Luna 10u-Prep C18(2) 100A (250×21.20 mm; 10 μm) column), ACN:H₂O/TFA was applied as eluent [ACN: acetonitrile; TFA: trifluoroacetic acid]. TFA was contained only in water in 0.005 M concentration. Yield: 0.2 g (74%). ¹H NMR [360 MHz, D₂O] δ 7.87 (1H, t, aromatic), 7.28 (2H, d, aromatic) 4.13 (4H, s, CH₂) 3.65 (4H, m, CH₂) 3.43-3.21 (8H, m, CH₂) 3.32 (4H, s, CH₂) 2.73 (8H, s, CH₂) 2.61 (4H, t, CH₂), 2.49 (2H, CH) 1.98-1.56 (12H, m, CH₂).

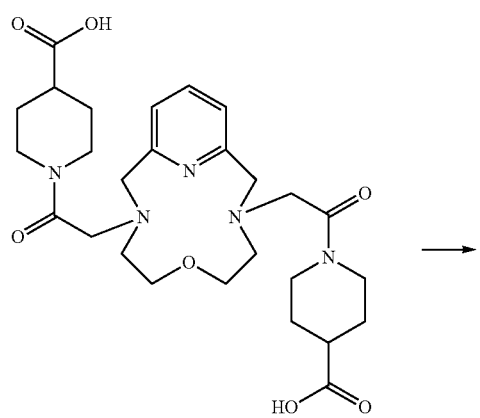

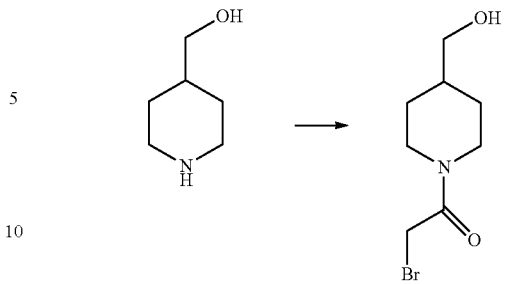

$^1$H NMR [360 MHz, CDCl$_3$] δ 1.61 (1H, m, CH) 1.71-1.30 (8H, m, CH$_2$), 3.52 (2H, m, (CH$_2$), 4.21 (2H, s, CH$_2$)

b.) Synthesis of tOPC2AM$^{PypCH2OH}$

The N-bromoacetyl-4-hydroymethyl piperidine obtained as described above (0.28 g, 1.20 mmol, 2.5 equivalent) was dissolved in dry acetonitrile and added dropwise to the acetonitrile solution (30 ml) of 6-oxa-3,9,15-triaza-bicyclo[9.3.1]pentadeca-1(14),11(15),12-triene (0.10 g, 0.48 mmol, 1 equivalent) and K$_2$CO$_3$ (0.2 g, 1.5 mmol, 3 equivalent) at room temperature within 30 minutes. Then the reaction mixture was refluxed in N2 atmosphere for 24 hours. After 24 hours, K$_2$CO$_3$ was filtered from the hot solution, and acetonitrile was evaporated at reduced pressure. The obtained crude product was purified with HPLC (Luna 10u-Prep C18(2) 100A (250×21.20 mm; 10 μm) column), ACN:H$_2$O/TFA was applied as eluent [ACN: acetonitrile; TFA: trifluoroacetic acid]. TFA was contained only in water in 0.005 M concentration. Yield: 0.17 g (69%).

EXAMPLE 9

Manufacture of tOPC2AM$^{PypCH2OH}$ a.) N-bromoacetyl-4-hydroxymethyl Piperidine Bromoacetyl bromide (3.56 g, 17.6 mmol, 1.55 ml, 1.5 equivalent), dry CH$_2$Cl$_2$ (50 ml) and K$_3$PO$_4$ (6.41 g, 30.2 mmol, 2.5 equ.) was mixed in a flask of 250 ml under N$_2$ atmosphere. 4-hydroxymethyl piperidine (1.34 g, 11.7 mmol, 1.0 equivalent) was dissolved in dry CH$_2$Cl$_2$ (20 ml) and was added dropwise to dichloromethane solution of bromoacetyl bromide at 0° C. in 30 minutes, then the reaction mixture was stirred for additional 12 hours at room temperature under N$_2$ atmosphere before the aqueous HCl solution (0.5 M, 30 ml) was added to the reaction mixture. After the addition of HCl solution, the reaction mixture was stirred for additional 5 minutes, then the two phases were separated using a separatory funnel. The aqueous phase was washed with CH$_2$Cl$_2$ (1×15 ml) and then the unified organic phases were washed with KHCO$_3$ solution (2×30 ml, 10 m/m %) and saturated NaCl solution (1×30 ml). The organic phase was dried with MgSO$_4$ then dichloromethane was evaporated at reduced pressure, and the crude product was stored at −20° C. until further use. Yield: 1.85 g (67%).

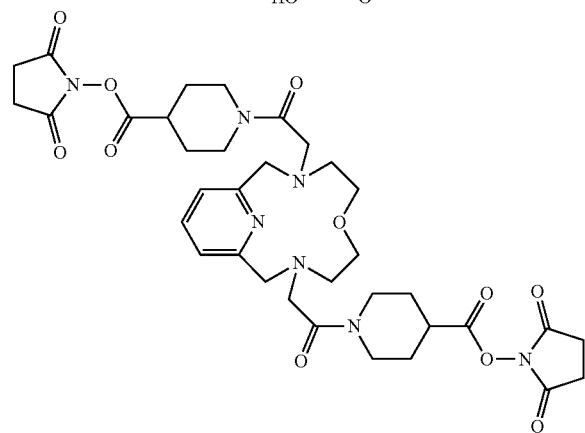

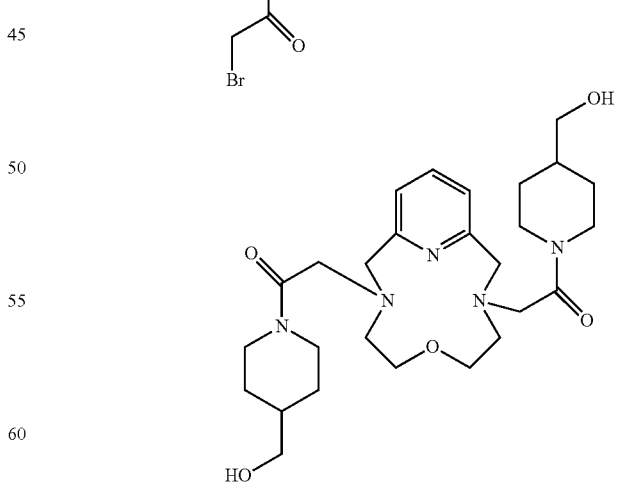

$^1$H NMR [360 MHz, D$_2$O] δ 7.91 (1H, t, aromatic), 7.41 (2H, d, aromatic) 4.10 (4H, s, CH$_2$) 3.56 (4H, d, CH$_2$) 3.58 (4H, m, CH$_2$) 3.48-3.22 (8H, m, CH$_2$) 3.36 (4H, s, CH$_2$) 2.62 (4H, t, CH$_2$), 1.64-1.32 (8H, m, CH$_2$) 1.55 (2H, m, CH).

EXAMPLE 10

Manufacture of tOPC2AM$^{PypBn}$ a). N-bromoacetyl-4-benzylpiperidine

Bromoacetyl bromide (3.56 g, 17.6 mmol, 1.55 ml, 1.5 equivalent), dry CH$_2$Cl$_2$ (50 ml) and K$_3$PO$_4$ (6.41 g, 30.2 mmol, 2.5 equ.) was mixed in a flask of 250 ml under N$_2$ atmosphere. 4-benzylpiperidine (2.05 g, 11.7 mmol, 1.0 equivalent) was dissolved in dry CH$_2$Cl$_2$ (20 ml) and was added dropwise to dichloromethane solution of bromoacetyl bromide at 0° C. in 30 minutes, then the reaction mixture was stirred for additional 12 hours at room temperature under N$_2$ atmosphere before the aqueous HCl solution (0.5 M, 30 ml) was added to the reaction mixture. After the addition of HCl solution, the reaction mixture was stirred for additional 5 minutes, then the two phases were separated using a separatory funnel. The aqueous phase was washed with CH$_2$Cl$_2$ (1×15 ml) and then the unified organic phases were washed with KHCO$_3$ solution (2×30 ml, 10 m/m %) and saturated NaCl solution (1×30 ml). The organic phase was dried with MgSO$_4$. then dichloromethane was evaporated at reduced pressure, and the crude product was stored at −20° C. until further use. Yield: 1.85 g (67%).

$^1$H NMR [360 MHz, CDCl$_3$] δ 1.91 (1H, m, CH) 1.69-1.24 (8H, m, CH$_2$) 2.66 (2H, m, CH$_2$) 4.23 (2H, s, (CH$_2$), 7.05-7.33 (5H, m, aromatic)

b.) tOPC2AM$^{PypBn}$ Synthesis

The N-bromoacetyl-4-benzylpiperidine obtained as described above (0.36 g, 1.20 mmol, 2.5 equivalent) was dissolved in dry acetonitrile and added dropwise to the acetonitrile solution (30 ml) of 6-oxa-3,9,15-triaza-bicyclo[9.3.1]pentadeca-1(14),11(15),12-triene (0.10 g, 0.48 mmol, 1 equivalent) and K$_2$CO$_3$ (0.2 g, 1.5 mmol, 3 equivalent) at room temperature within 30 minutes. Then the reaction mixture was refluxed in N$_2$ atmosphere for 24 hours. After 24 hours, K$_2$CO$_3$ was filtered from the hot solution, and acetonitrile was evaporated at reduced pressure. The obtained crude product was purified with HPLC (Luna 10u-Prep C18(2) 100A (250×21.20 mm; 10 µm) column), ACN:H$_2$O/TFA was applied as eluent [ACN: acetonitrile; TFA: trifluoroacetic acid]. TFA was contained only in water in 0.005 M concentration. Yield: 0.17 g (55%).

$^1$H NMR [360 MHz, D$_2$O] δ 7.95 (1H, t, aromatic), 7.65 (4H, m, aromatic) 7.25-7.20 (6H, m, aromatic) 7.22 (2H, d, aromatic) 4.04 (4H, s, CH$_2$) 3.67 (4H, m, CH$_2$) 3.47-3.21 (8H, m, CH$_2$) 3.34 (4H, s, CH$_2$) 2.62 (4H, d, CH$_2$) 2.49 (4H, t, CH$_2$) 1.92 (2H, m, CH) 1.71-1.31 (8H, m, CH$_2$).

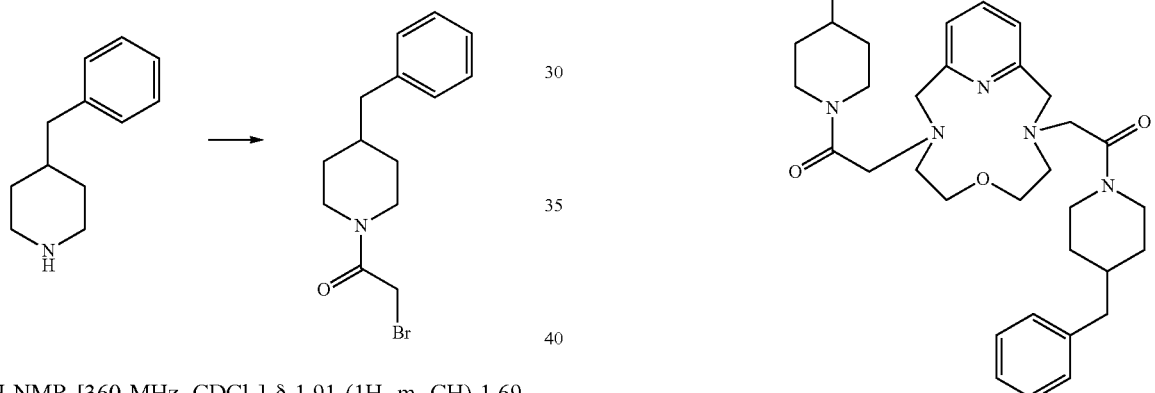

EXAMPLE 11

Manufacture of tOPC2AM$^{PypBnNO2}$ a.) N-bromoacetyl-4-(4'-nitrobenzyl)piperidine

Bromoacetyl bromide (3.56 g, 17.6 mmol, 1.55 ml, 1.5 equivalent), dry CH$_2$Cl$_2$ (50 ml) and K$_3$PO$_4$ (6.41 g, 30.2 mmol, 2.5 equ.) was mixed in a flask of 250 ml under N$_2$ atmosphere. 4-(4'-nitrobenzyl)piperidine (2.57 g, 11.7 mmol, 1.0 equivalent) was dissolved in dry CH$_2$Cl$_2$ (20 ml) and was added dropwise to dichloromethane solution of bromoacetyl bromide at 0° C. in 30 minutes, then the reaction mixture was stirred for additional 12 hours at room temperature under N$_2$ atmosphere before the aqueous HCl solution (0.5 M, 30 ml) was added to the reaction mixture. After the addition of HCl solution, the reaction mixture was stirred for additional 5 minutes, then the two phases were separated using a separatory funnel. The aqueous phase was washed with CH$_2$Cl$_2$ (1×15 ml) and then the unified organic phases were washed with KHCO$_3$ solution (2×30 ml, 10 m/m %) and saturated NaCl solution (1×30 ml). The organic phase was dried with MgSO₄, then dichloromethane was evaporated at reduced pressure, and the crude product was stored at −20° C. until further use. Yield: 2.43 g (61%).

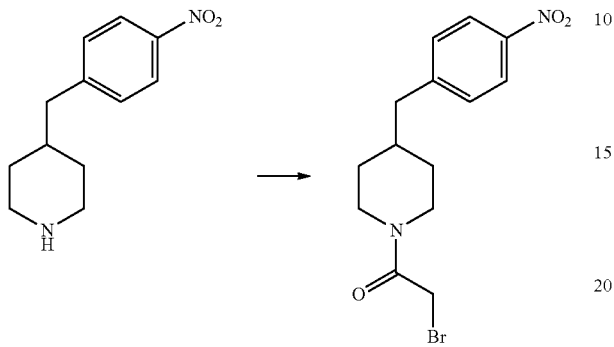

¹H NMR [360 MHz, CDCl₃] δ 1.90 (1H, m, CH) 1.62-1.33 (8H, m, CH₂) 2.56 (2H, m, CH₂) 4.21 (2H, s, (CH₂), 7.40-8.3 (4H, m, aromatic)

b). Synthesis of tOPC2AM$^{PypBnNO2}$

A The N-bromoacetyl-4-(4'-nitrobenzyl)piperidine obtained as described above (0.41 g, 1.20 mmol, 2.5 equivalent) was dissolved in dry acetonitrile and added dropwise to the acetonitrile solution (30 ml) of 6-oxa-3,9,15-triazabicyclo[9.3.1]pentadeca-1(14),11(15),12-triene (0.10 g, 0.48 mmol, 1 equivalent) and K₂CO₃ (0.2 g, 1.5 mmol, 3 equivalent)) at room temperature within 30 minutes. Then the reaction mixture was refluxed in N₂ atmosphere for 24 hours. After 24 hours, K₂CO₃ was filtered from the hot solution, and acetonitrile was evaporated at reduced pressure. The obtained crude product was purified with HPLC (Luna 10u-Prep C18(2) 100A (250×21.20 mm; 10 μm) column), ACN:H₂O/TFA was applied as eluent [ACN: acetonitrile; TFA: trifluoroacetic acid]. TFA was contained only in water in 0.005 M concentration. Yield: 0.21 g (61%).

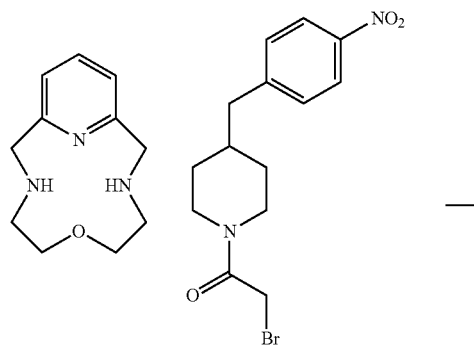

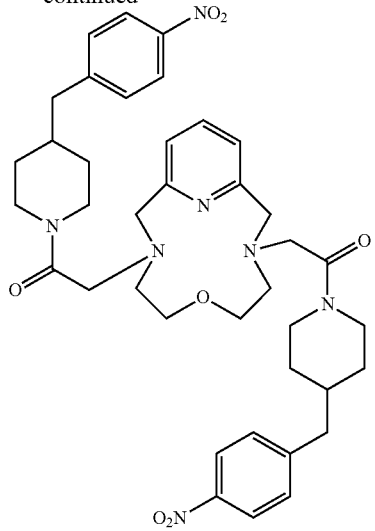

¹H NMR [360 MHz, D₂O] δ 8.3 (4H, m, aromatic) 7.85 (1H, t, aromatic), 7.52 (4H, m, aromatic) 7.31 (2H, d, aromatic) 4.11 (4H, s, CH₂) 3.54 (4H, m, CH₂) 3.50-3.32 (8H, m, CH₂) 3.29 (4H, s, CH₂) 2.63 (4H, d, CH₂) 2.56 (4H, t, CH₂) 1.92 (2H, CH) 1.62-1.29 (8H, m, CH₂)

c). Preparation of tOPC2AM$^{PypBnNH2}$

The above obtained tOPC2AM$^{PypBnNO2}$ (0.4 g, 0.55 mmol) was dissolved in dry methanol, 0.04 g Pd-carbon catalyst was added, and then the mixture was reduced under 1 bar hydrogen pressure at room temperature for 2 hours. The catalyst was removed by filtration, the filtrate was evaporated at reduced pressure. Yield: 0.33 g (91%).

¹H NMR [360 MHz, D₂O] δ 7.92 (1H, t, aromatic), 7.31 (2H, d, aromatic) 7.15 (4H, m, aromatic) 6.68 (4H, m, aromatic) 4.11 (4H, s, CH₂) 3.58 (4H, m, CH₂) 3.42-3.38 (8H, m, CH₂) 3.29 (4H, s, CH₂) 2.62 (4H, d, CH₂) 2.62 (4H, t, CH₂) 1.91 (2H, m, CH) 1.89 (2H, CH) 1.62-1.32 (8H, m, CH₂)

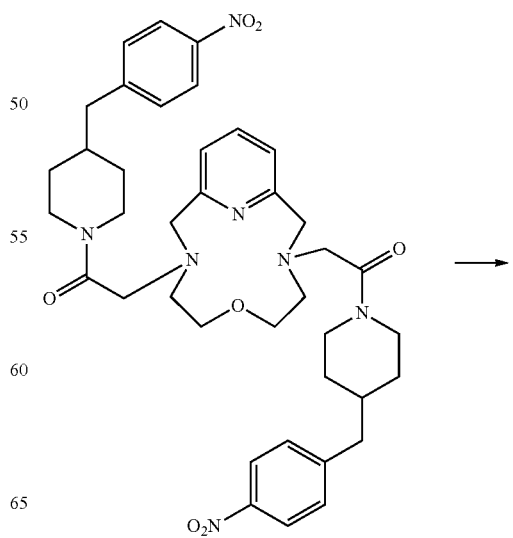

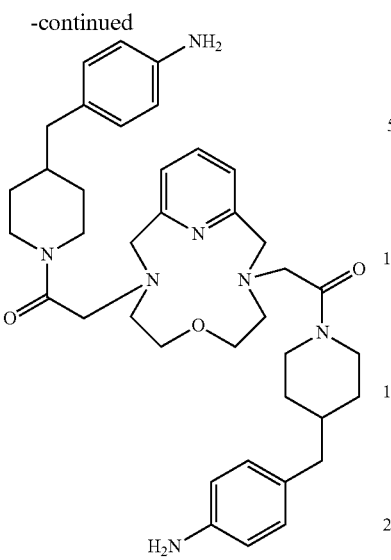

d). Synthesis of tOPC2AM$^{PypBnNCS}$

The tOPC2AM$^{PypBnNH2}$ (0.20 g, 0.30 mmol, 1.0 equivalent) obtained as described above was dissolved in chloroform (50 ml) and cooled to 0° C., then solution of $K_2CO_3$ prepared with 30 ml water was added (0.09 g, 0.60 mmol, 2 equivalent) and thiophosgene (0.07 g, 0.60 mmol, 2 equivalent) solution prepared with 30 ml chloroform was also added. Then the mixture was allowed to warm up to room temperature for 5 hours. The organic phase was separated, washed with water (1×10 ml), dried on $MgSO_4$, and then the chloroform was evaporated at reduced pressure. The obtained crude product was purified with HPLC (Luna 10u-Prep C18(2) 100A (250×21.20 mm; 10 μm) column), ACN:$H_2O$/TFA was applied as eluent [ACN: acetonitrile; TFA: trifluoroacetic acid]. TFA was contained only in water in 0.005 M concentration. Yield: 0.17 g (74%).

$^1$H NMR [360 MHz, $D_2O$] δ 8.10 (1H, t, aromatic), 7.41-7.31 (8H, m, aromatic) 7.32 (2H, d,) 4.11 (4H, s, $CH_2$) 3.52 (4H, m, $CH_2$) 3.45-3.31 (8H, m, $CH_2$) 3.31 (4H, s, $CH_2$) 2.62 (4H, d, $CH_2$) 2.61 (4H, t, $CH_2$) 1.88 (2H, m, CH) 1.95 (2H, CH) 1.62-1.41 (8H, m, $CH_2$).

EXAMPLE 12

Synthesis of pOH-tOPC2AM$^{Pyp}$

The 2-bromo-1-(piperidine-1-yl)ethanone (0.30 g, 1.45 mmol, 2.5 equivalent) was dissolved in dry acetonitrile, and then added dropwise at room temperature to the acetonitrile solution (30 ml) of 6-oxa-3,9,15-triaza-bicyclo[9.3.1]pentadeca-1(14),11(15),12-triene-13-ol (0.13 g, 0.58 mmol, 1 equivalent) and $K_2CO_3$ (0.24 g, 1.75 mmol, 3 equivalent) within 30 minutes (the macrocycle was manufactured according to the papers K. M. Lincoln, M. E. Offutt, T. D. Hayden, R. E. Saunders, K. N. Green, Inorg Chem., 2014. 53(3), 1406-1416. and K. M. Lincoln, P. Gonzalz, T. E: Richardson, D. A. Julovich, R. Saunders, J. W. Simpkins, K. N. Green, Chem. Commun., 2013. 49(26), 2712-2714 substituting the agent used for cyclisation to bis-(2-tosylaminoethyl)-ether). Then the reaction mixture was refluxed in $N_2$ atmosphere for 24 hours. After 24 hours, $K_2CO_3$ was filtered from the hot solution, and the filtrate was evaporated at reduced pressure. The obtained crude product was purified with HPLC (Luna 10u-Prep C18(2) 100A (250×21.20 mm; 10 Lm) column), ACN:$H_2O$/TFA was applied as eluent [ACN: acetonitrile; TFA: trifluoroacetic acid]. TFA was contained only in water in 0.005 M concentration. Yield: 0.16 g (50%).

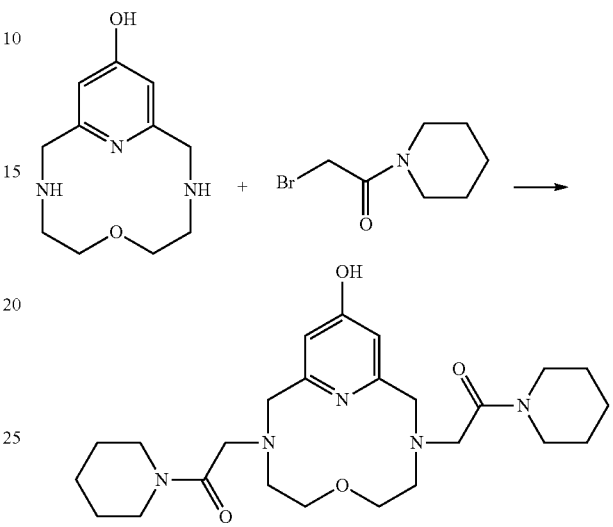

$^1$H NMR [360 MHz, $D_2O$] δ 1.51 (12H, m, (6 db $CH_2$)), 3.2 (2H, m, ($CH_2$)), 3.3-3.50 (8H, m, (4 db $CH_2$)), 3.87 (2H, m, ($CH_2$)), 4.65 (4H, m, (2 db $CH_2$)), 4.81 (4H, s, (2 db $CH_2$), 6.42 (2H, s, (CH) aromatic);

$^{13}$C NMR [100 MHz, $D_2O$] δ 23.4 2 db $CH_2$; 25.0 2 db $CH_2$; 25.5 2 db $CH_2$; 43.9 4 db $CH_2$; 46.1 2 db $CH_2$; 57.8 2 db $CH_2$; 60.1 2 db $CH_2$; 64.2 2 db $CH_2$; 113.1 2 db CH aromatic; 153.3 C(OH) aromatic; 158.3 2 db C aromatic; 161.8 2 db C(=O);

EXAMPLE 13

Manufacture of OMe-tOPC2AM$^{Pyp}$

The 2-bromo-1-(piperidine-1-yl)ethanone (0.28 g, 1.38 mmol, 2.5 equivalent) was dissolved in dry acetonitrile, and then added dropwise at room temperature to the acetonitrile solution (30 ml) of 6-oxa-3,9,15-triaza-13-methoxy-bicyclo[9.3.1]pentadeca-1(14),11(15),12-triene (0.13 g, 0.55 mmol, 1 equivalent) and $K_2CO_3$(0.23 g, 1.65 mmol, 3 equivalent) within 30 minutes (the macrocycle was synthesized according to the following papers: K. M. Lincoln, M. E. Offutt, T. D. Hayden, R. E. Saunders, K. N. Green, Inorg, Chem., 2014, 53(3), 1406-1416, and K. M. Lincoln, P. Gonzalz, T. E: Richardson, D. A. Julovich, R. Saunders, J. W. Simpkins, K. N. Green, Chem. Commun., 2013, 49(26), 2712-2714). Then the reaction mixture was refluxed in $N_2$ atmosphere for 24 hours. After 24 hours, $K_2CO_3$ was filtered off from the hot solution, and the filtrate was evaporated under reduced pressure. The obtained crude product was purified by HPLC (Luna 10u-Prep C18(2) 100A (250×21.20 mm; 10 m) column), ACN:$H_2O$/TFA was applied as eluent [ACN: acetonitrile; TFA: trifluoroacetic acid]. TFA was contained only in water in 0.005 M concentration. Yield: 0.16 g (60%).

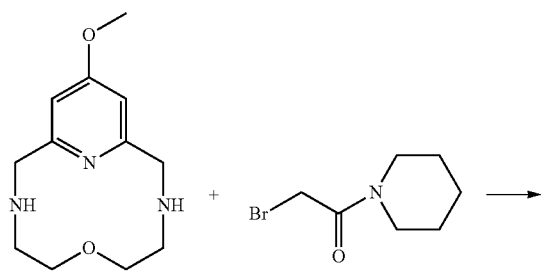

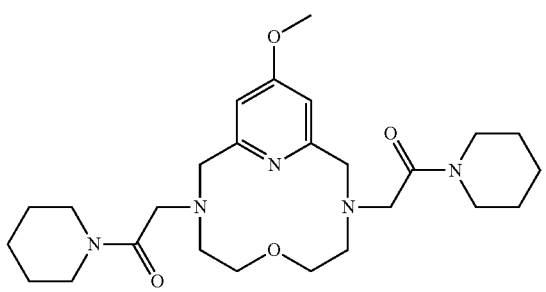

¹H NMR [360 MHz, D₂O] δ1.47 (12H, m, (6 db CH₂)), 3.17 (2H, m, (CH₂)), 3.28-3.47 (8H, m, (4 db CH₂)), 3.78 (3H, s, CH₃), 3.85 (2H, m, (CH₂)), 4.63 (4H, m, (2 db CH₂)), 4.78 (4H, s, (2 db CH₂), 6.88 (2H, s, (CH) aromatic);

¹³C NMR [100 MHz, D₂O] δ 24.0 2 db CH₂; 25.1 2 db CH₂; 25.2 2 db CH₂; 43.9 4 db CH₂; 46.3 2 db CH₂; 56.3 1 db CH₃; 57.7 2 db CH₂; 60.2 2 db CH₂; 64.8 2 db CH₂; 110.1 2 db CH aromatic; 111.4 C(OCH₃) aromatic; 158.7 2 db C aromatic; 161.8 2 db C(=O).

EXAMPLE 13

Efficacy Data

During the physico-chemical studies of tOPC2A, tOPC2M$^{Pyp}$ and tOPC2M$^{Pro}$ compounds prepared according to Example 1, 2, and 5, their protonation constants, as well as equilibrium behaviour and kinetic inertness of their Mn(II) complexes was studied in detail, and the characteristic relaxivity values of the complexes were determined in the presence and absence of HSA (Human Serum Albumin), at 25 and 37° C. and physiological pH. All studies were performed in the presence of 0.15 M NaCl, the same concentration as that of the electrolyte under physiological conditions.

The results of equilibrium study are summarized in Table 1, in addition to the protonation constants, total basicity of ligands and stability constants of their Mn(II) complexes, the pMn value calculated for complexes are also represented in the table.

TABLE 1

Protonation constants and total basicity of the studied ligands, stability constants of their Mn(II) complexes and calculated pMn values (25° C., 0.15M NaCl).

| | $logK_1$ | $logK_2$ | $logK_3$ | $logK_4$ | $\Sigma logK_i^H$ | $logK_{MnL}$ | pMn |
|---|---|---|---|---|---|---|---|
| tOPC2A | 7.73(2) | 7.66(1) | 2.13(1) | — | 17.52 | 13.03(1) | 8.59 |
| tOPC2AM$^{Pyp}$ | 7.91(2) | 5.51(3) | — | — | 13.42 | 10.84(4) | 7.60 |
| tOPC2AM$^{Pro}$ | 7.37(3) | 5.14(4) | 3.26(4) | 2.40(4) | 18.17 | 10.03(1) | 7.37 | pMn values were calculated by using the equilibrium constants at pH = 7.4 and cMn = cL = 10⁻⁵ M Based on the pMn values presented in Table 1 (calculated using the equilibrium constants at pH=7.4 and cMn=cL=10⁻⁵ M), it can be concluded that the studied Mn(II) complexes are formed in 100% at physiological pH, which is an essential aspect of the practical use.

An important parameter of using Mn(II) containing contrast agents in vivo is the low kinetic reactivity of the complex. The kinetic reactivity is generally tested with metal ion exchange reactions, where the replacing metal ion is Zn(II) or Cu(II) in most of the cases. The application of Cu(II) is advantageous for more reasons, in one hand the complexes with ligands are of great thermodynamic stability, so relatively small excess of Cu(II) ion leads to complete replacement, on the other hand molar absorbance values of Cu(II) complexes both in UV and visible range are sufficiently high to enable spectrophotometric method for examinations even at low concentrations. Moreover, the endogenic character of the Cu(II) ion provides additional information on in vivo processes. Replacement reactions were executed with at least 10-fold excess Cu(II) ion concentration to ensure pseudo-first order conditions.

Dissociation reactions of Mn(H) complexes may take place in several pathways as represented below.

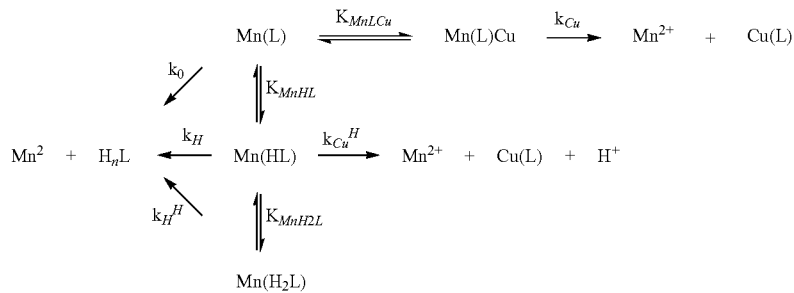

The $k_0$, $k_H$, $K_H^H$, $k_{Cu}$ and $k_{Cu}^H$, rate constants indicate the spontaneous, proton associated, metal assisted and proton-metal assisted (when the replacing metal ion attacks the protonated complex) reaction pathways of the complex. The $K_{MnHL}$, $K_{MnH_2L}$ and $K_{MnLCu}$ are stability constants of the protonated and binuclear intermediate complexes.

In case of metal complexes formed with macrocyclic ligands the above detailed mechanism involves only proton associated dissociation pathways (in some instances spontaneous dissociation may have some role), since the formation of binuclear complexes are inhibited (denticity of rigid ligands does not exceed the coordination number of the metal ion, $Mn^{2+}$). Due to this reason, replacement reactions were executed in 2.0-5.0 pH range with only 10-fold Cu(II) replacement metal ion excess.

In general the $k_{obs}$ pseudo-first order rate constants obtained in each reaction are given with the following equation, where the stability constants of each reaction pathway and that of the forming intermediate are also considered:

$$k_{obs} = \frac{k_0 + k_1[H^+] + k_2[H^+]^2 + k_3[Cu^{2+}] + k_4[Cu^{2+}][H^+]}{1 + K_{MnHL}[H^+] + K_{MnH_2L}[H^+]^2 + K_{MnLCu}[Cu^{2+}]}, \quad (1)$$

whereas $K_{MnHL}=[Mn(HL)]/[Mn(L)][H^+]$, $K_{MnH_2L}=[Mn(H_2L)]/[Mn(HL)][H^+]$, $K_{MnLCu}=[Mn(L)M]/[Mn(L)][M]$, $k_1=k_H \cdot K_{MnHL}$, $k_2=k_H^H \cdot K_{MnH_2L}$, $k_3=k_{Cu} \cdot K_{MnLCu}$, $k_4=k_{Cu}^H \cdot K_{MnHL}$ Results of the kinetic study showed that in the dissociation of [Mn(tOPC2A)], [Mn(tO2PC2AM$^{Pyp}$)]$^{2+}$ and [Mn(tO2PC2AM$^{Pro}$)] complexes, the proton associated dissociation (characterized with $k_1$) plays an important role. Using these rate constants the half-life ($t_{1/2}$) of [Mn(tOPC2A)], [Mn(tO2PC2AM$^{Pyp}$)] and [Mn(tO2PC2AM$^{Pro}$)] complexes dissociation may be calculated at physiologic pH, being $1.67 \times 10^3$, $1.07 \times 10^5$ and $1.17 \times 10^4$ hours, respectively.

In order to estimate the quantity of complex decomposing in the body, it is useful to handle elimination and complex dissociation as parallel, primary reaction characterized by the (2) equation set for $Gd^{3+}$ complexes [F. K. Kálmán and G. Tircsó, Inorg. Chem., 2012, 51, 10065]:

$$[GdL]_d = \frac{k_d}{k_d + k_{ex}}[GdL]_0\left(1 - e^{-(k_d+k_{ex})t}\right) \quad (2)$$

The equation indicates that dissociation degree of the complex depends on the ration of rate constants. For the (renal) elimination of contrast agent 1.6 hour half life can be given in general, characterized by a $k_{ex}=0.433$ h$^{-1}$ rate constant. Using the $k_d$ values of Mn(II) complexes and the $k_{ex}$ values characteristic for elimination, one can calculate the percentile ratio of injected complex dissociated in vivo until complete elimination (12-24 hours). Calculation verified, that less than 0.1% of the of [Mn(tOPC2A)], [Mn(tO2PC2AM$^{Pyp}$)]$^{2+}$ and [Mn(tO2PC2AM$^{Pro}$)] complexes would dissociate before the elimination of the complex. Considering the endogenic characteristic of Mn(II) complexes and its negligible amount it cannot cause significant burden for MRI tested patients. Considering the new results, during the in vivo dissociation (37° C.) of [Gd(DTPA)]$^{2-}$ complex (Magnevist) applied in practice, 2.2% Gd(III) ion releases being 4.4-fold of the value calculated on the basis of experiments at 25° C.[Sarka L. et al, Chem. Eur. J., 2000, 6, 719]. Using this approach one can estimate the quantity of the Mn(II) released in vivo for the presented Mn(II) complexes which appears to be less than 0.5%. This value is definitely less than the values for some of the Gd$^{3+}$-based contrast agents applied in practice. [Baranyai Z. et al, Chem. Eur. J., 2015, 21, 4789]

In addition to appropriately low kinetic reactivity, complexes shall also have suitable relaxivity for the purpose of practical use (relaxivity (mM$^{-1}$s$^{-1}$): relaxation rate increase of 1 mM solution of the paramagnetic substance compared to the measured value under diamagnetic conditions [Tóth É., et. al., The Chemistry of Contrast Agents in Medical Magnetic Resonance Imaging, Chichester: John Wiley & Sons, 2001.]). Higher complex relaxivity results in higher contrast increasing effect, meaning that the same image quality is obtained by introducing less amount of complex with higher relaxivity. The relaxivity value of both complexes were determined at pH=7.4 and 25 and 37° C. in the presence and absence of HSA (Human Serum Albumin, c=0.7 mM) to better stimulate conditions of the in vivo application. Relaxivity values of the complexes are presented in Table 2. Comparing the data in Table 2 with the relaxivity values of DOTAREM ([Gd(DOTA)]$^-$ complex, $r_1$=3.83 mM$^{-1}$s$^{-1}$) and MAGNEVIST ([Gd(DTPA)]$^{2-}$ complex, $r_1$=4.02 mM$^{-1}$s$^{-1}$) [Powell, D. H., Ni Dhubhghaill, O. M., Pubanz, D. et al. (1996) J. Am. Chem. Soc., 118, 9333-9346] applied in practice under the same conditions, the Mn(II) complexes presented herein obviously have higher relaxivity as well as higher contrast enhancing effect.

TABLE 2

Relaxivity values (20 MHz) of the $Mn^{2+}$ complexes prepared and studied (pH = 7.4) in the presence and absence of 0.7 mM HSA at 25 and 37° C.

| Komplex | T (° C.) | $r_1$ ($mM^{-1}s^{-1}$) | $r_1$ ($mM^{-1}s^{-1}$) HSA |
|---|---|---|---|
| [Mn(tOPC2A)] | 25 | 3.20 | 4.60 |
|  | 37 | 2.70 | 3.89 |
| [Mn(tOPC2AM$^{Pyp}$)]$^{2+}$ | 25 | 4.77 | 8.92 |
|  | 37 | 3.77 | 7.00 |
| [Mn(tOPC2AM$^{Pro}$)] | 25 | 5.27 | 6.14 |
|  | 37 | 3.93 | 4.68 |

The invention claimed is:

1. A compound of general formula (I)

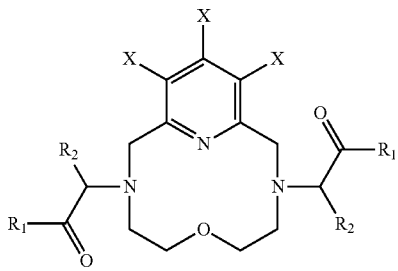

(I)

where $R_1$=—OH or —$NR_3R_4$, where:
  a) —$NR_3R_4$ is a heterocycle of 4 to 7 members, or
  b) $R_3$ is H, alkyl, aryl, nitroaryl, aminoaryl, or isothiocyanate-aryl and $R_4$ is H, alkyl, or –$(CH_2)_n$–COOH, where n ranges from 1 to 10, $R_2$ is H, alkyl having 1 to 6 carbon, aryl, nitroaryl, aminoaryl, or isothiocyanate-aryl, and X is H, —$CH_3$, —COOH, —OH, —$OCH_3$, alkoxy-, —$NO_2$, —$NH_2$, —NCS, —NHS-activated ester, alkyl, or aryl, where aryl is unsubstituted or substituted with hydroxyl, hydroxyalkyl, nitro, amino, or isothiocyanate.

2. The compound according to claim 1, wherein the compound is 3,9-bis[2-oxo-2-2-(piperidine-1-yl)-ethyl] 6-oxa-3,9,15-triaza-bicyclo[9.3.1]pentadeca-1(14),11(15),12-triene.

3. A complex comprising the compound of claim 1 and a metal selected from Mn(II), Fe(II), Fe(III), Co(II), and Ni(II).

4. A method of imaging, comprising:
applying a compound according to claim 1 as a contrast agent in diagnostic imaging, and
performing diagnostic imaging.

5. A contrast agent kit, comprising: a compound according to claim 1.

6. A complex comprising the compound of claim 2 and a metal selected from Mn(II), Fe(II), Fe(III), Co(II), and Ni(II).

7. A method of imaging, comprising:
applying a compound according to claim 2 as a contrast agent in diagnostic imaging, and
performing diagnostic imaging.

8. A method of imaging, comprising:
applying a compound according to claim 3 as a contrast agent in diagnostic imaging, and
performing diagnostic imaging.

9. A contrast agent kit, comprising: a compound according to claim 2.

10. A contrast agent kit, comprising: a compound according to claim 3.

11. A method of imaging, comprising:
applying a complex according to claim 6 as a contrast agent in diagnostic imaging, and
performing diagnostic imaging.

12. A contrast agent kit, comprising: a complex according to claim 6.

13. A compound of general formula (I)

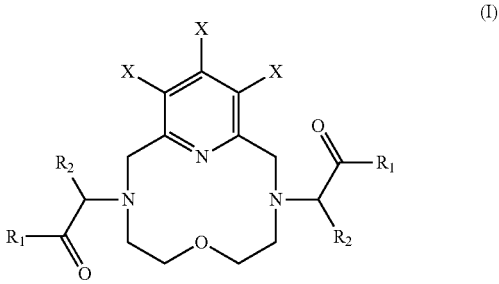

(I)

where $R_1$ is —$NR_3R_4$, where the —$NR_3R_4$ forms a heteroaryl-ring having 5 to 7 carbon optionally substituted with —COOH, —OH, —$OCH_3$, —$NO_2$, —$NH_2$, —NCS, —NHS-activated ester, aryl having 5 to 7 carbon, amino-, or isothiocyanate, $R_2$ is H, alkyl having 1 to 6 carbon, aryl, nitroaryl, aminoaryl, or isothiocyanate-aryl, and X is H, —$CH_3$, —COOH, —OH, —$OCH_3$, alkoxy-, —$NO_2$, —$NH_2$, —NCS, —NHS-activated ester, alkyl, or aryl, where aryl is unsubstituted or substituted with hydroxyl, hydroxyalkyl, nitro, amino, or isothiocyanate.

14. A method of imaging, comprising:
applying a compound according to claim 13 as a contrast agent in diagnostic imaging, and
performing diagnostic imaging.

15. A contrast agent kit, comprising: a compound according to claim 13.

16. A complex comprising the compound of claim 13 and a metal selected from Mn(II), Fe(II), Fe(III), Co(II), and Ni(II).

17. A compound of general formula (I)

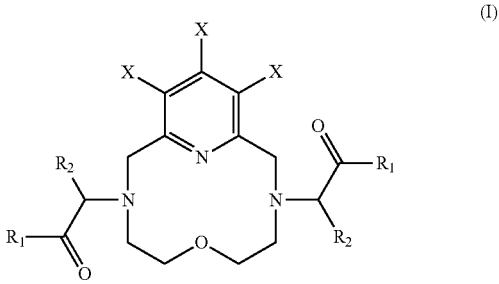

(I)

where
$R_1$ is selected from:

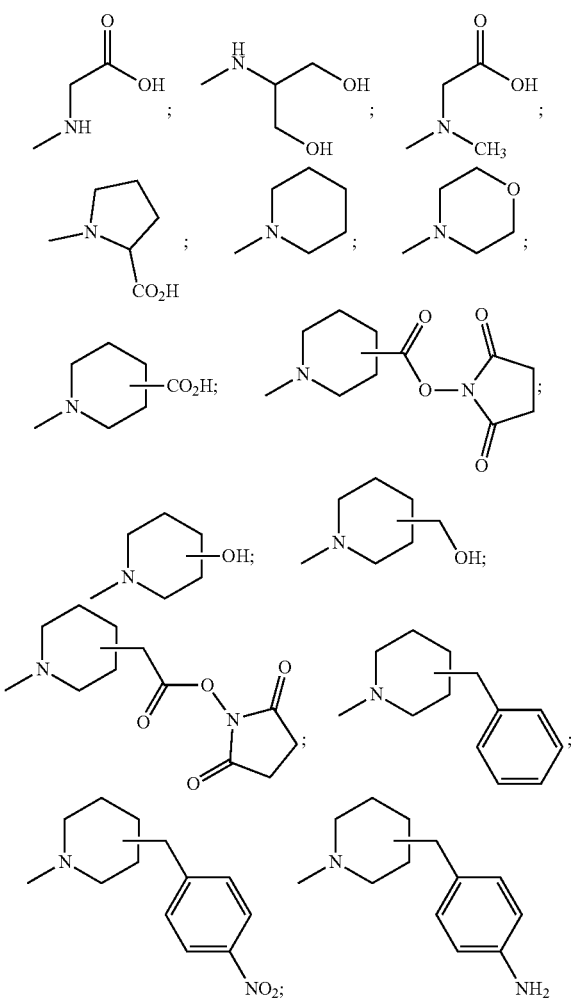

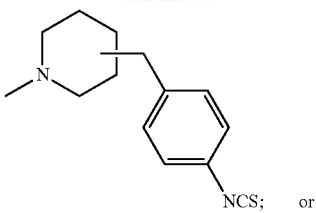

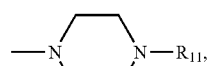

wherein $R_{11}$ is H, carboxyl-, or alkyl-carbonyl, $R_2$ is H, alkyl having 1 to 6 carbon, aryl, nitroayl, aminoaryl, or isothiocyanate-aryl, and X is H, —$CH_3$, —COOH, —OH, —$OCH_3$, alkoxy-, —$NO_2$, —$NH_2$, —NCS, —NHS-activated ester, alkyl, or aryl, where aryl is unsubstituted or substituted with hydroxyl, hydroxyalkyl, nitro, amino, or isothiocyanate.

18. A method of imaging, comprising:
applying a compound according to claim 17 as a contrast agent in diagnostic imaging, and
performing diagnostic imaging.

19. A contrast agent kit, comprising: a compound according to claim 17.

20. A complex comprising the compound of claim 17 and a metal selected from Mn(II), Fe(II), Fe(III), Co(II), and Ni(II).

* * * * *